United States Patent [19]

Sakai et al.

[11] 4,438,377

[45] Mar. 20, 1984

[54] STOP CONTROL CIRCUIT FOR BRUSHLESS DC MOTOR

[75] Inventors: Masaaki Sakai; Mitsugu Yoshihiro, both of Atsugi, Japan

[73] Assignee: Sony Corporation, Tokyo, Japan

[21] Appl. No.: 270,219

[22] Filed: Jun. 4, 1981

[30] Foreign Application Priority Data

Jun. 6, 1980 [JP] Japan ................................. 55-76806

[51] Int. Cl.³ ............................................ H02K 29/02
[52] U.S. Cl. .................................... 318/254; 318/258; 318/369
[58] Field of Search .................... 318/254, 254 A, 138, 318/258, 366, 368, 369, 608

[56] References Cited

U.S. PATENT DOCUMENTS

| 3,571,683 | 3/1971 | Prezzi et al. | 318/258 |
| 3,596,160 | 7/1971 | Rakes | 318/258 X |
| 3,600,659 | 8/1971 | Danchuk | 318/608 |
| 3,928,836 | 12/1975 | Makino et al. | 338/32 R |
| 3,946,292 | 3/1976 | Tanikoshi | 318/254 A |
| 4,053,829 | 10/1977 | Maruo | 324/46 |
| 4,070,606 | 1/1978 | Morozumi et al. | 318/254 A |
| 4,079,360 | 3/1978 | Ookubo et al. | 365/158 |

FOREIGN PATENT DOCUMENTS

978,255 4/1972 Canada .
1060987 8/1979 Canada .

Primary Examiner—B. Dobeck
Attorney, Agent, or Firm—Lewis H. Eslinger; Alvin Sinderbrand

[57] ABSTRACT

A stop control circuit for a DC motor causes the motor to stop precisely by purely electrical action. A DC motor is provided with a bidirectional driving circuit, a servo circuit for controlling the driving circuit, and a rotation detector associated with the motor shaft to provide a phase signal that depends, in magnitude and polarity, on the particular rotational angle of the shaft, regardless whether the motor is turning. A stop control circuit then includes an amplifier whose output varies according to the phase signal, and a switch that normally provides the servo signal to the driving circuit, but, upon command, switches over to provide thereto the output of the amplifier as a brake signal. Alternatively the rotation detector can include two sensor elements separated by $\pi/2$, and the stop control circuit can include an inverting amplifier, a non-inverting amplifier coupled to one of the sensor elements, and a switch circuit with inputs coupled respectively to these amplifiers. A comparator provides a switch signal to the switch circuit in dependence on the phase signal from the other sensor element. In another embodiment, a differential amplifier provides a brake signal in dependence upon both the phase signals from the two sensor elements.

15 Claims, 16 Drawing Figures

MOTOR PHASE

MOTOR PHASE

STOP CONTROL CIRCUIT FOR BRUSHLESS DC MOTOR

BACKGROUND OF THE INVENTION

1. Field of the Invention

This invention relates to a motor control circuit for a brushless DC motor, and, more particularly, relates to a stop control circuit, or braking circuit for the DC motor. Specifically, this invention is directed to a circuit which, by purely electrical means, can cause the DC motor to stop precisely.

2. Brief Description of the Prior Art

In a conventional DC brushless motor, either a mechanical brake or an electromechanical brake is used for stopping the motor. These mechanical and electromechanical brakes have a distinct disadvantage in that the braking force applied to the motor varies drastically with variations in the mechanical load and with temperature changes. In addition, as the motor and the associated brake age and wear, the amount of braking force tends to vary.

One arrangement of such conventional motors imposes a mechanical braking load at all times during operation. While such arrangement does permit the motor to be stopped quickly, it has a severe drawback in that a constant braking force has to be overcome to drive the motor, and additional power is consumed in overcoming this force, even when the motor is operated at a constant rotational speed.

Alternatively, a brushless DC motor can be arranged with a mechanical brake that is applied only at stopping. While this has the desirable advantage of eliminating the need for power to overcome any constant braking force, it has the disadvantage in that moving parts, which can wear and break down, are required. In addition, a solenoid plunger or the like is required to drive the braking mechanism. The arrangement including the plunger is somewhat bulky and cumbersome, and must be carefully constructed to be sufficiently reliable, as the plunger must be ready at all times, although it is required only upon braking.

If the brushless DC motor is used, for example, as a capstan motor in a video tape recorder (VTR) used for tape editing, the stopping point of the motor must be determined precisely. Thus, if an electromechanical brake is used, the time of application of the plunger for driving the brake mechanism must be determined with great accuracy. This usually requires precise manual adjustment.

If a mechanical brake is used with such a capstan motor, it is possible that the stop position thereof can be shifted due to shifts in external forces, such as tape back tension. In such case, the motor will tend to stop at an incorrect position. Therefore, these conventional braking systems have the disadvantage that the stop position, even though having been correctly adjusted initially, will tend to vary subsequently.

OBJECTS AND SUMMARY OF THE INVENTION

Accordingly, it is an object of this invention to provide a motor stop control circuit for a DC motor which avoids the drawbacks of the aforementioned prior-art arrangements.

It is another object of this invention to provide a motor stop control circuit which uses a purely electrical circuit arrangement to determine the precise stopping point of a motor.

It is still another object of this invention to provide a motor stop control circuit which is of simple design, and which can stop the associated motor quickly and precisely.

It is a further object of this invention to provide a motor stop control circuit suitable for use in a VTR, and which will facilitate accurate editing of a video tape thereon.

In accordance with an aspect of this invention, a drive control circuit is provided for use with a brushless DC motor having a bidirectional-rotation driving circuit applying current in either of two opposite directions to the motor, a servo circuit providing a servo output signal to the driving circuit to control the phase and speed of the motor, and a rotation detector associated with the shaft of the motor and providing to the servo circuit a phase signal whose magnitude and polarity indicate the electrical rotational angle of the motor shaft. Such a drive control circuit includes a stop control circuit formed of an amplifier circuit that has an input coupled to the rotation detector and an output providing an output voltage that varies with the phase signal, and a controllable switch with a normally-closed input coupled to the servo circuit and a normally-open input coupled to the amplifier circuit. The output of the controllable switch is connected to the bidirectional-rotation driving circuit. In normal operation, the controllable switch provides the servo output signal to the driving circuit, but, upon a stop command, instead applies the output voltage from the amplifier to the driving circuit to stop the motor.

In an alternative embodiment the rotation detector can include a first and second detector element displaced from each other by an electrical angle that is an odd multiple of $\pi/2$. The amplifier circuit can then include an inverting amplifier and a non-inverting amplifier, each having an input coupled to the first detector element, a switching circuit with inputs respectively coupled to the output of the inverting amplifier and to the output of the non-inverting amplifier, and an output connected to the normally-open input of the controllable switch. The stop control circuit also includes a comparator having an input coupled to the second detector element and an output coupled to a control terminal of the switching circuit. This arrangement will provide two stable stopping points for each electrical rotational angle of $2\pi$. In yet another arrangement according to this invention, the amplifier circuit is formed of a differential amplifier having differential inputs respectively coupled to the first and second detector elements and an inverter coupled to the output of the differential amplifier. A switching circuit has inputs coupled to the output of the differential amplifier and to the output of the inverter, and has an output coupled to the normally-open input of the controllable switch. The first and second detector elements are connected, through an adding network, to a comparator, which then provides a switching signal to the switching circuit. This arrangement avoids any error which might occur owing to DC offset in the first and second detector elements.

These and further objects, features, and advantages of the stop control circuit of this invention will become apparent from the ensuing description of several preferred embodiments thereof, when read in conjunction with the accompanying drawings.

DETAILED DESCRIPTION OF THE PREFERRED EMBODIMENTS

Figure 1:
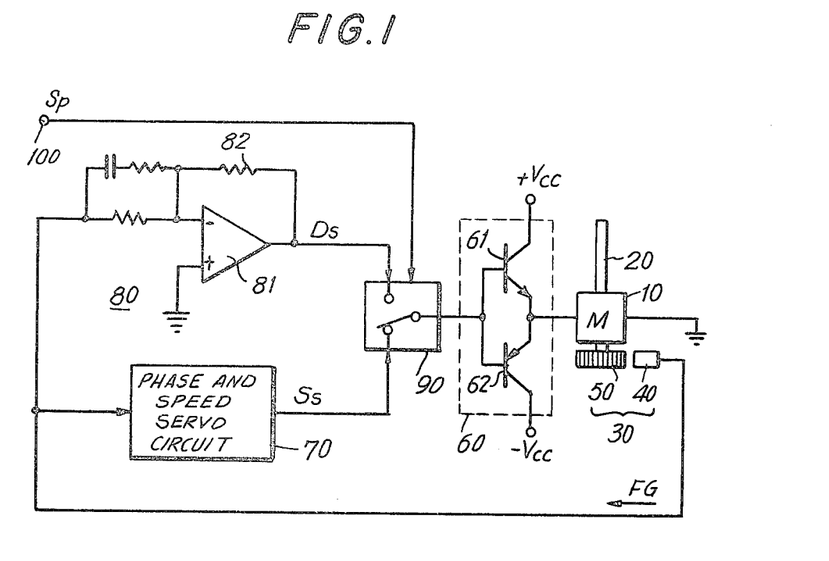
FIG. 1 is a circuit diagram of a first embodiment of the present invention.

With reference to the drawings, and initially to FIG. 1, a brushless DC motor 10 is showing having a shaft 20 defining the rotational axis of the motor 10. A motor-shaft angular displacement-detection assembly 30 is formed of a sensor mechanism 40 and a rotary signalling device 50 mounted on the shaft 20. In this embodiment, the sensor 40 is a magnetoresistive device and the rotary signaling device 50 is a rotary signal magnet. One example of the detection assembly 30 is the magnetoresistive arrangement sold by Sony Corporation under the trademark DME, and described, for example, in U.S. Pat. No. 4,053,829 to T. Maruo. Alternative arrangements of the angular displacement detection assembly 30 could include an optical angular detector or an arrangement including a Hall-effect detector as the sensor 40. Any equivalent detection assembly could be used, provided that the sensor 40 is capable of providing motor phase information, for instance, as a DC level, even if the motor is stopped.

A bidirectional-rotation drive circuit 60 is coupled to the armature of the motor 10. In this embodiment, the drive circuit 60 includes an NPN transistor 61 and a PNP transistor 62 connected in series. The bases of the transistors 61 and 62 are connected together to form an input terminal, and the emitters thereof are connected together to the armature of the motor 10. The collector of the transistor 61 is connected to a positive voltage supply $+V_{cc}$ while the collector of the transistor 62 is coupled to a negative voltage supply $-V_{cc}$.

Figure 2A:
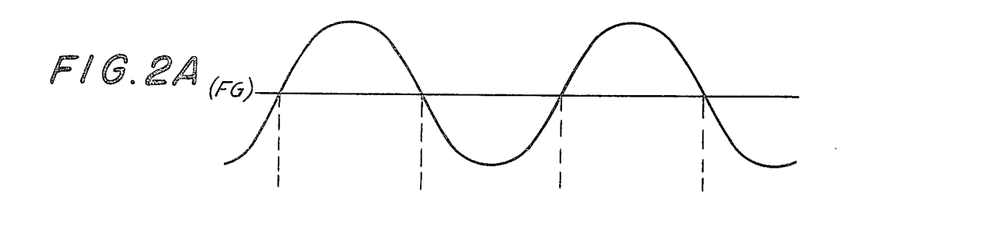
FIG. 2A and 2B are waveform charts used for explaining the operation of the embodiment of FIG. 1.

A servo circuit 70, which can be of any convenient conventional design, has an input coupled to the sensor 40 and an output normally coupled to the input of the drive circuit 60 to provide a servo signal $S_s$ thereto. As shown in FIG. 2A, the sensor 40 provides a sinusoidal output signal, or phase signal FG, whose level varies generally as the sine of the electrical rotational angle of the shaft 20. The servo circuit 70 provides the servo signals $S_s$ in response to the phase signal FG such that the phase and speed of the motor 10 is properly controlled when the motor is driven in either the forward or reverse direction.

In this embodiment, a brake control circuit 80 includes an inverting amplifier formed of an operational amplifier 81 and a biasing net 82 connected thereto. The operational amplifier 81 has a plus input coupled to ground, and a minus input coupled through the net 82 to the output thereof and also to the sensor 40 to receive the phase signal FG. The output of the operational amplifier 81 then provides a braking signal $D_s$, which is generally the inverse of the phase signal FG. A controllable switch 90 is disposed in advance of the drive circuit 60 and has an output coupled to the input of the drive circuit 60. The switch 90 also has a normally-closed input coupled to the output of the servo circuit 70 and a normally-open input coupled to the output of the amplifier 81. A stop control signal input 100 is connected to a control terminal of the switch 90 so that a stop control signal $S_p$ can be applied thereto for precisely braking the motor 10.

As mentioned heretofore, the phase signal FG, as shown in FIG. 2A, varies sinusoidally, with the motor phase, such that it has a zero value at electrical angles of, e.g. 0, $\pi$, $2\pi$, etc. The phase signal FG has positive values for motor phases between 0 and $\pi$, between $2\pi$ and $3\pi$, and at regular intervals thereafter. Likewise, the phase signal FG has negative values at the intervening intervals, namely, between $\pi$ and $2\pi$, and succeeding alternate intervals.

Figure 2B:
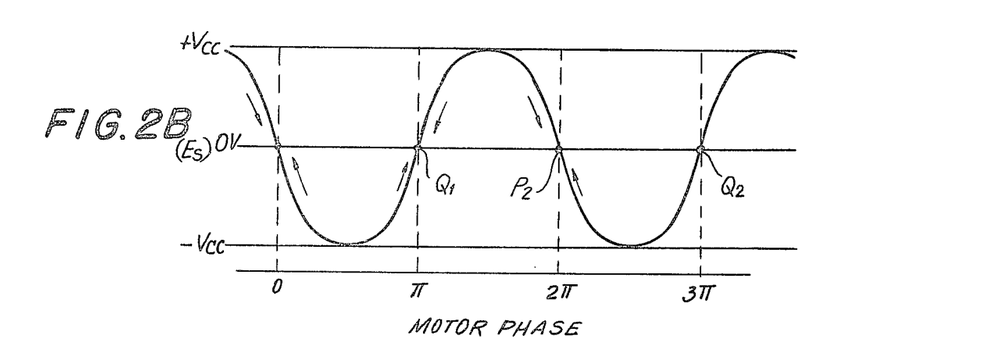

As shown in FIG. 2B, when the stop control signal $S_p$ is applied at the terminal 100, and the braking signal $D_s$ is applied to the input terminal of the drive circuit 60, the drive voltage $E_s$ applied to the stator of the motor 10 is inversely proportional to the value of the phase signal FG.

Particularly, as the braking signal $D_s$ is a sinusoidal signal with an average level of 0 volts, the transistor 61 is turned on for alternate (positive) half cycles, and the transistor 62 is turned on for the intervening (negative) half cycles.

Because the average DC level of the voltage ES is zero, the motor 10 will stop quickly. Further, because the applied voltage $E_s$ is 0 at the zero-crossing points $P_1$, $Q_1$, $P_2$, $Q_2$ (FIG. 2B), the motor will tend to come to rest at one of those points.

It should be apparent that the arrangement as described herein and as shown in FIG. 1, will, upon a stop control signal $S_p$, cause the motor 10 to stop quickly, and will cause it to stop precisely at one of the aforementioned zero-crossing points.

Here it is assumed that the motor is being stopped after having been driven in the positive, or forward direction.

In the neighborhood of the zero-crossing points $P_1$, $P_2$, etc., corresponding to electrical angles of 0, $2\pi$, etc., deviations from those zero-crossing points will cause the drive voltage $E_s$ to be applied in the sense to drive the motor back towards those zero-crossing positions $P_1$, $P_2$, etc. In other words, in the vicinity of the positions $P_1$, $P_2$, etc., greater amounts of deviation will cause correspondingly greater currents to flow in the stator, and the rotor magnets of the DC motor will be attracted more strongly to return to the positions $P_1$, $P_2$, etc.

However, in the neighborhood of the alternate zero-crossing positions $Q_1$, $Q_2$, etc., the voltages tend to change in the opposite sense, so that the greater the amount of deviation of the motor shaft from such zero-crossing positions $Q_1$, $Q_2$, etc., the more strongly the rotor magnets of the motor 10 will be repelled from those positions $Q_1$, $Q_2$, etc.

Consequently, the motor 10 will tend to stop at the positions $P_1$, $P_2$, etc., but will not stop at the positions $Q_1$, $Q_2$, etc. Therefore, for each cycle, i.e., for one rotational electrical angle of $2\pi$, the embodiment of FIG. 1 provides a single stable stopping point $P_1$, $P_2$, etc.

At the stopping points $P_1$, $P_2$, etc., it should be noted that the drive current $E_s$ is maintained at zero volts. Thus, when the motor is stopped, no current is consumed by the driving circuit 60.

Further, in the embodiment of FIG. 1, so long as the stop control signal $S_p$ is applied at the terminal 100, the motor is maintained at a stable stopping position $P_1$, $P_2$, etc. The motor will be held precisely at such position $P_1$, $P_2$, even if a noise signal occurs in the circuitry including the sensor 40 and the operational amplifier 81, and the motor will not rotate from its stopped position.

Figure 3:
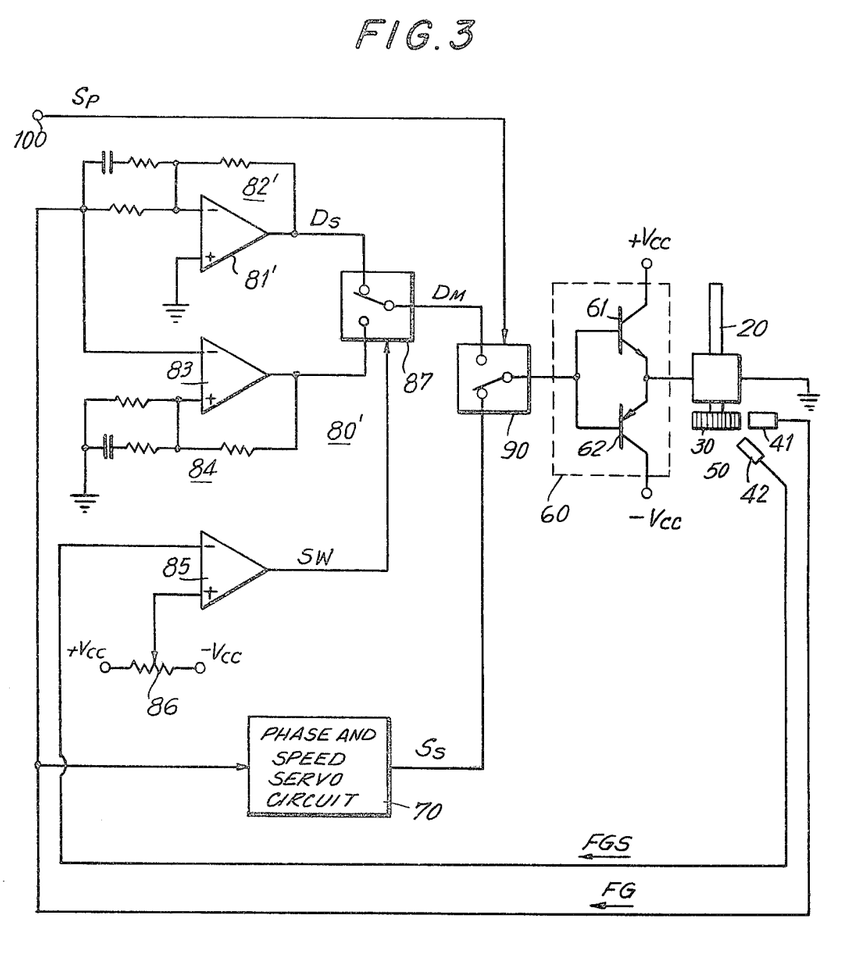
FIG. 3 is a circuit diagram showing a second embodiment of this invention.

FIG. 3 shows another embodiment of this invention which provides two stable stop positions for each cycle, i.e., for each rotation of $2\pi$ of electrical angle.

Elements in FIG. 3 corresponding to similar elements in the embodiment of FIG. 1, are identified with the same reference numerals and a detailed description thereof is omitted.

Figure 4A:
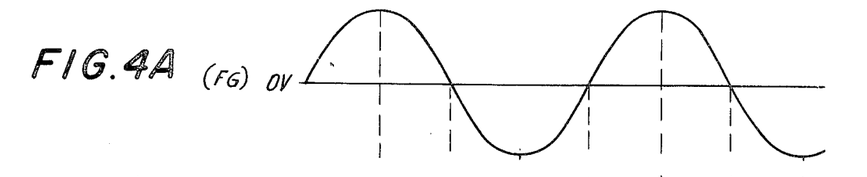
FIG. 4A–4F are waveform charts used in explaining the operation of the embodiment of FIG. 3.
Figure 4B:
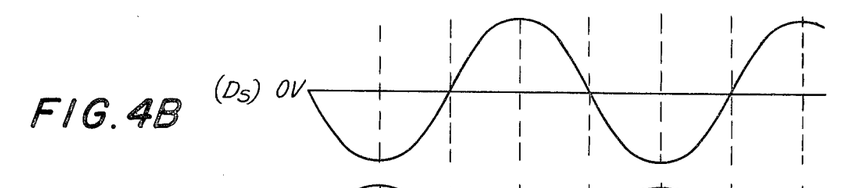
Figure 4C:
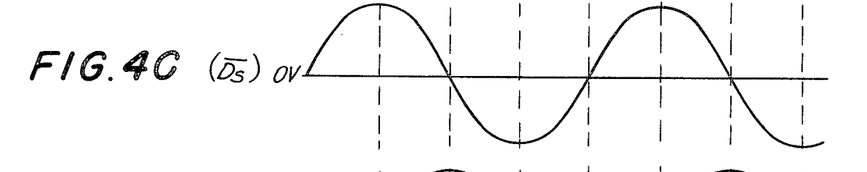
Figure 4D:
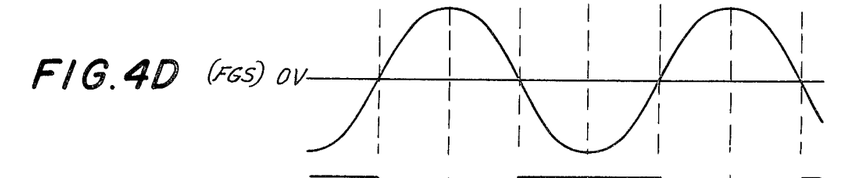
Figure 4E:
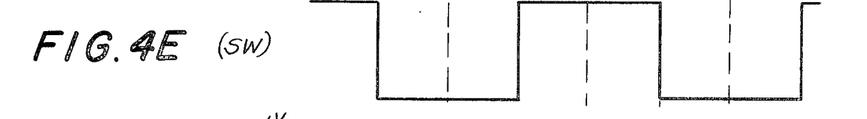

In the FIG. 3 embodiment, a pair of position sensor elements 41 and 42 are provided disposed at an electrical angular separation of 90° or $\pi/2$. It should be recognized however, that these sensor elements 41 and 42 could be arranged at any odd multiple thereof, such as 270° ($3\pi/2$) or 450° ($5\pi/2$). The sensor element 41, similar to the sensor 40 in the foregoing embodiment, provides the phase signal FG, as shown in FIG. 4A, which varies as the sine of the electrical angle of the rotor shaft 20. The sensor element 42 supplies a second, or supplemental phase signal FGS, as shown in FIG. 4D, which lags the phase signal FS by 90° or $\pi/4$ in electrical angle.

The brake control circuit 80' includes an inverter formed of an operational amplifier 81' and a bias net 82', arranged generally similarly to the corresponding elements in FIG. 1. The operational amplifier 81' receives the phase signal FG at its minus input, and provides an inverted output signal $D_s$, as shown in FIG. 4, at its output. A non-inverting amplifier is arranged in parallel with the inverting amplifier, and is formed of an operational amplifier 83 and a bias net 84 coupled thereto. The operational amplifier 83 has its plus input coupled to receive the phase signal FG and has its minus input coupled through the bias net 84 to its output and to ground. The output of the non-inverting amplifier 83, 84 provides a non-inverted output signal $\overline{D_s}$, as shown in FIG. 4C.

The brake control circuit 80' further includes a comparator, here formed of an operational amplifier 85. This operational amplifier 85 has its minus input coupled to the sensor element 42 to receive the second phase signal FGS and has plus input coupled to receive a reference potential. In this embodiment, the reference potential is applied from the slider of a variable resistor or potentiometer 86 whose resistive element is coupled between the positive voltage supply $+V_{cc}$ and the negative voltage supply $-V_{cc}$. The output terminal of the comparator operational amplifier 85 provides a switching signal SW (FIG. 4E) which is high when the second phase signal FGS is below the reference voltage provided from the slider of the resistor 86, and is low whenever the phase signal FGS exceeds that reference voltage. As can be understood by comparing FIGS. 4A and 4E, the switching signal SW changes values from high to low at the positive peaks of the phase signal FG, and changes from low to high at the negative peaks thereof.

The variable resistor 86 is provided so that the reference voltage applied to the plus input of the comparator operational amplifier 85 can be adjusted in the sense to compensate for any DC offset voltage.

A switching circuit 87 is further provided having respective input terminals coupled to the outputs of the operational amplifiers 81' and 83, a control terminal coupled to the output of the comparator operational amplifier 85, and an output coupled to provide a brake signal $D_M$ to an input terminal of the controllable switch 90.

Figure 4F:
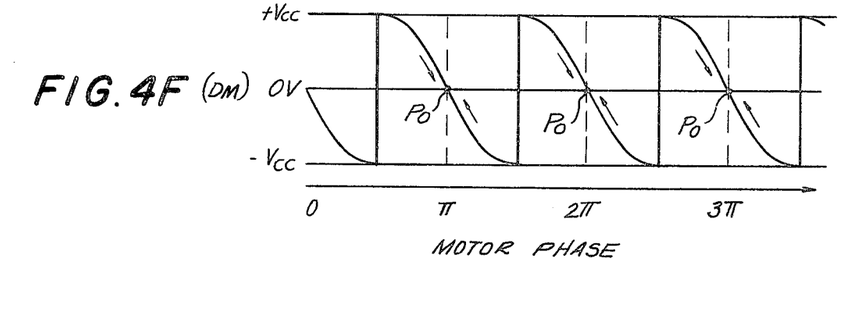

In this embodiment, the brake signal $D_M$ is formed from alternate sections of the inverted signals $D_S$ and the non-inverted signal $\overline{D_S}$, as illustrated in FIG. 4F. In other words, because the switching signal SW changes over midway between the zero-crossing points of the signals $D_S$ and $\overline{D_S}$, the resulting brake signal $D_M$ has a generally sawtooth form whose level changes from positive to negative each time the zero-crossing points $P_0$ are reached. The brake signal $D_M$ also has an average DC value of 0, so that the resulting drive current from the drive circuit 60 will also be zero whenever the stop control signal $S_p$ is applied at the input 100. Therefore, the motor will be caused to stop quickly and will come to rest at one of the stop points $P_0$, as shown in FIG. 4F.

Moreover, because there are two stop points for every complete cycle representing an electrical angle of $2\pi$, the motor 10 can be stopped with greater precision than with the foregoing embodiment of FIG. 1. In other words, because the drive voltage $E_S$ from the drive circuit 60 will be applied, during a braking operation, in the sense to drive the rotor 20 towards the nearest zero-crossing point, all such zero-crossing points $P_0$ are stable stopping positions.

Figure 5:
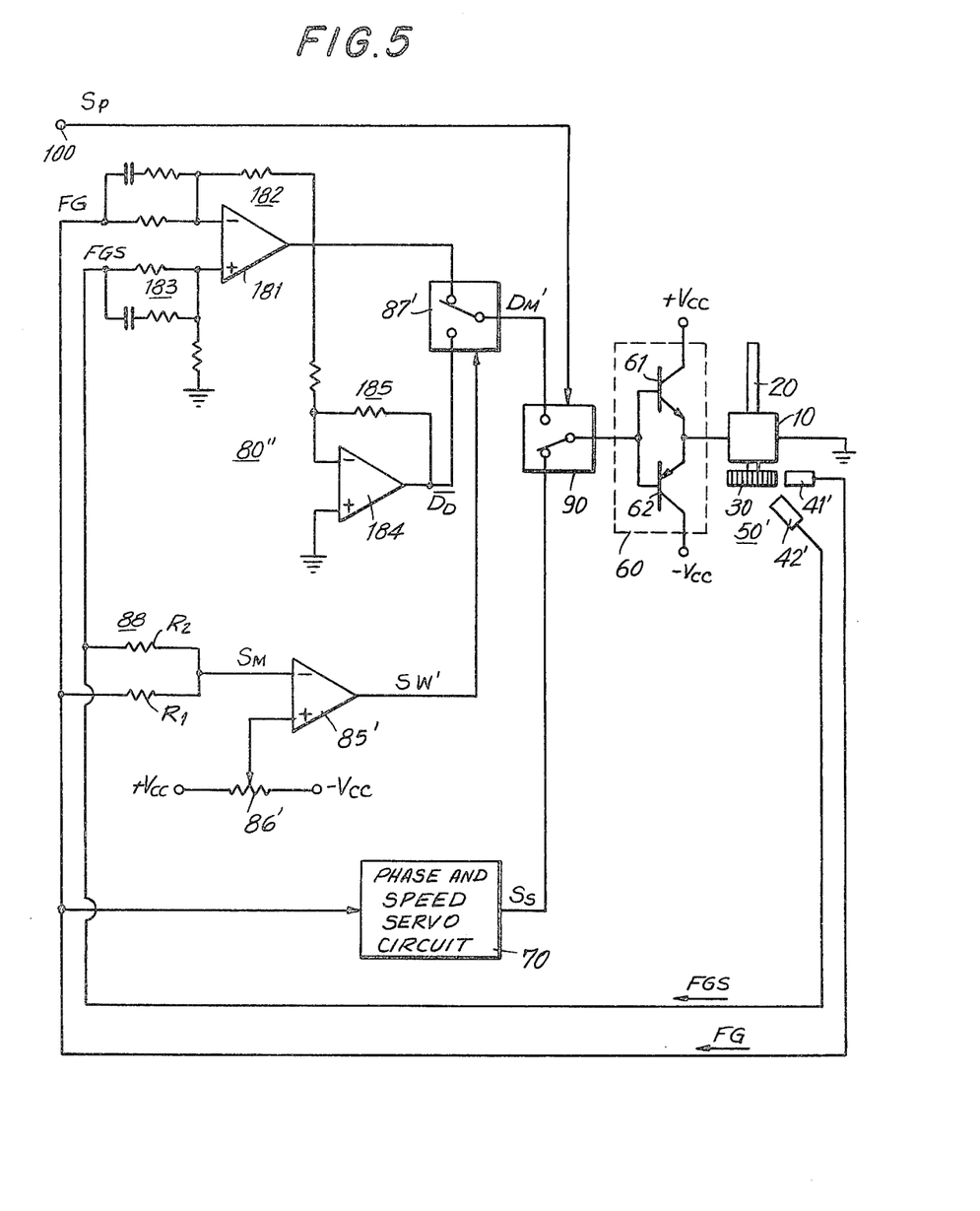
FIG. 5 is a circuit diagram showing a third embodiment of this invention.

Yet another embodiment of this invention is illustrated in FIG. 5, in which elements similar to those shown in the foregoing embodiments are identified with the same reference characters, and for which a detailed description is omitted. In this embodiment, as in the foregoing embodiment of FIG. 3, two sensor elements 41' and 42' are provided to furnish respective phase signals FG and FGS, separated in phase from one another by an odd multiple of $\pi/2$. In this embodiment, the phase signals FG and FGS are differentially combined to provide the braking signal $D'_M$, and the sensor elements 41' and 42' are disposed an electrical angle of $\pi/4$ ahead of the zero position of the rotor shaft 20, and $\pi/4$ behind that position, respectively.

The brake control circuit 80'' is arranged herein to provide a brake signal $D'_M$ in dependence on both phase signals FG and FGS, in a fashion which will tend to eliminate any error due to DC offset voltage in the magnetic flux sensor elements 41' and 42', thereby minimizing the need to manually adjust the circuit, either by the manufacturer or by the user.

Figure 6A:
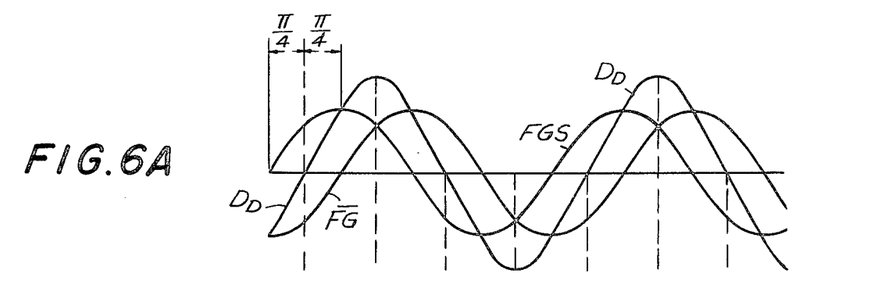
FIGS. 6A–6E are waveform charts used in explaining the operation of the embodiment of FIG. 5.

The brake control circuit 80'' includes an operational amplifier 181 arranged as a differential amplifier. A bias net 182 is coupled to the sensor element 41', to the minus input of the operational amplifier 181, and to the output thereof, while a bias net 183 is coupled to the sensor element 42', to the plus input of the operational amplifier 181, and the ground. As a result, the operational amplifier provides at its output terminal a difference signal $D_D$, as shown in FIG. 6A. This output signal $D_D$ can be represented as $$D_D = FGS - FG - \overline{FSG} + \overline{FG},$$

where $\overline{FG}$ represents the inverse of the phase signal FG. It should be noted that the output signal $D_D$ leads the inverse of the phase signal $\overline{FG}$ by 45°, but lags the phase signal FGS by a similar 45°.

Figure 6B:
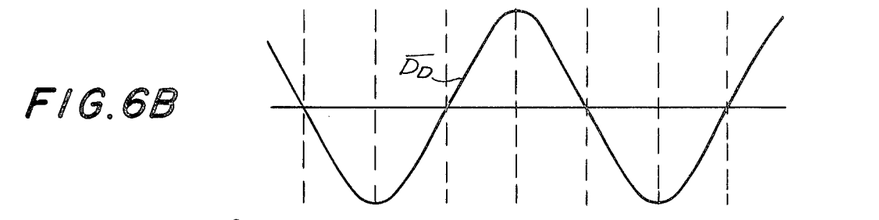
Figures 6C, 6D:
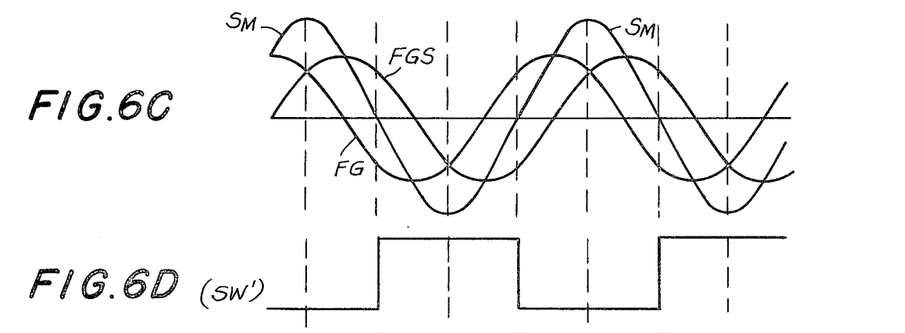
Figure 6E:
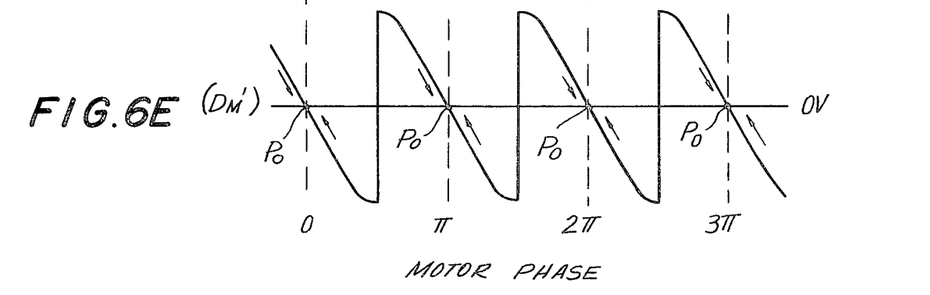

An inverted amplifier formed of an operational amplifier 184 and a bias net 185, and the minus terminal of the amplifier 184 is coupled to receive the output signal $D_D$ from the output of the operational amplifier 181. The operational amplifier 184 provides at its own output terminal an inverted output signal $D_D$, as shown in FIG. 6B. The output signal $D_D$ is applied to one input terminal of a switch circuit 87', while the inverted output signal $\overline{D}_D$ is applied to the other input terminal thereof. A comparator operational amplifier 85' is arranged in a fashion similar to the corresponding comparator operational amplifier of FIG. 3, to provide a switching signal SW' to the input terminal of the switch circuit 87'. This operational amplifier 85' has its plus terminal connected to the slider of a variable resistor 86' arranged to permit adjustment of its switchover point to compensate for any DC offset voltages. The minus input of the operational amplifier 85' is coupled through a resistive adder net 88 to both the sensor elements 41' and 42'. This net 88 is formed of equal-value resistors $R_1$ and $R_2$, respectively coupling the minus input terminal of the amplifier 85' to the sensor elements 41' and 42'. As a result, a sum signal $S_M$ formed of the sum of the phase signals FG and FGS, as shown in FIG. 6C, is provided to the minus terminal of the comparator operational amplifier 85'. This sum signal $S_M$ is separated in phase by $\pi/2$ from each of the output signal $D_D$ and the inverted output signal $D_D$, and, therefore the sum signal $S_M$ has zero-crossing points at extremes of the signals $D_D$ and $D_D$. Consequently, the switching signal SW' provided from the output of the comparator operational amplifier 85' is high during the period that the output signal $D_D$ is decreasing from its positive extreme to its negative extreme, and is low when the inverted output signal $D_D$ is decreasing from its positive extreme to its negative extreme. Consequently, the switch circuit 87' provides the generally sawtooth brake signal $D'_M$, as shown in FIG. 6E. As with the foregoing embodiment of FIG. 3, the embodiment of FIG. 5 assures that the motor 10 will be stopped quickly, at either of two stopping points $P_0$ in each rotational cycle of $2\pi$ electrical angle. Further, because the difference between the two phase signals FG and FGS is used to provide the output signals $\overline{D}_D$ and $D_D$, even if the phase signals FG and FGS include any DC offset voltage, the effect of such offset voltage will be eliminated to a great extent.

Experiments performed by the inventors in this case have indicated that the motor 10 will indeed stop within the first few cycles of the phase signal FG, once the stop control signal $S_p$ is applied at the terminal 100. Further, if the embodiments of FIGS. 3 and 5 are used, so that the number of stable stop points $P_0$ is increased, the motor 10 will be stopped even more quickly. With any of the foregoing embodiments of FIGS. 1, 3, or 5, stopping of the motor 10 can be effected by purely electrical action, without need to resort to any mechanical or electromechanical braking devices. As a result, the braking effect achieved according to this invention will not change either with temperature or with age of the equipment, as is the case with mechanical and electromechanical braking techniques. Consequently, stopping control can be carried out with great consistency and accuracy.

In addition, once the motor 10 is stopped, the rest position will not change, even if an external noise signal somehow occurs.

Furthermore, with the braking technique according to this invention, the ultimate rest positions $P_0$, or $P_1$, $P_2$, etc., are separated by equal rotational angles. Consequently, the rotary angle of the motor shaft 20 between one stop position and the next is always constant. Therefore, stopping the motor 10 at a desired location can be performed easily and with precision. As a result, if the motor stop control circuit of this invention is applied to the capstan motor of a VTR, the same can be used for video tape editing in a precise, yet uncomplicated fashion.

Furthermore, it is apparent that a motor using a stop control circuit according to this invention can be used as a stepping drive without any difficult modifications.

Also, the circuit of this invention has the effect of reducing power consumption, because electric current does not flow from the drive circuit 60 when the motor is stopped at one of the stable stopping points $P_0$, or $P_1$, $P_2$, etc.

It is, of course, also possible to arrange the circuit according to this invention with an additional switch circuit, similar to the switch circuit 87 or 87', arranged between the controllable switch 90 and the drive circuit 60. In such case, a DC voltage would be applied to one of the inputs of the additional switch circuit so that a braking torque, i.e., a torque applied in the reverse rotational direction, would be applied to the motor 10. The additional switch circuit would normally be conditioned to supply the output of the controllable switch 90 to the drive circuit 60. However, when a stop command signal $S_p$ is initially applied, the additional switch circuit would be switched over to the DC voltage to apply a braking torque to the motor. After a short interval, when the rotating speed of the motor 10 drops below a predetermined speed, the additional switch circuit would be switched back to the normal input, and the stop control operation as mentioned for any of the foregoing embodiments could be performed.

Further, the phase signals FG and FGS need not be generated exclusively by magnetic means. That is, it is possible, for example, to determine the rotational position of the motor shaft 20 optically or electrostatically, so long as the rotational detector will provide a DC output signal to indicate the rotational phase of the motor 10 even if the motor is stopped.

Although several particular embodiments of this invention have been described in detail herein with reference to the accompanying drawings, it to be understood that the invention is not limited to those precise embodiments and that various changes and modifications may be effected therein by persons skilled in the art without departing from the scope or spirit of the invention as defined in the appended claims.

What is claimed is:

1. A drive control circuit for a brushless DC motor comprising bidirectional-rotation driving circuit means for applying current in either of two opposite directions to said motor; servo circuit means providing a servo output signal for said driving circuit means to control the phase and speed of said motor; rotation detecting means for providing a phase signal whose magnitude and polarity indicate the electrical rotational angle of said motor; amplifier means amplifying said phase signal and providing an output voltage that varies according to said phase signal; and controllable switching means having a first condition for normally providing said servo output signal to said driving circuit means, and a second condition for applying said output voltage to said driving circuit means in a sense to brake said motor.

2. A drive control circuit according to claim 1, wherein said phase signal is also provided to said servo circuit means to control the same, and said amplifier means includes an inverting amplifier.

3. A drive control circuit for a brushless DC motor comprising bidirectional-rotation driving circuit means for applying current in either of two opposite directions to said motor; servo circuit means providing a servo output signal for said driving circuit means to control the phase and speed of said motor; rotation detecting means for providing a phase signal to said servo circuit means to control the same and having magnitude and polarity to indicate the electrical rotational angle of said motor; amplifier means amplifying said phase signal and providing an output voltage that varies according to said phase signal, said amplifier means including an inverting amplifier having an operational amplifier with a plus input connected to a fixed reference voltage, a minus input coupled to receive said phase signal, and an output providing said output voltage; and controllable switching means having a first condition for normally providing said servo output signal to said driving circuit means, and a second condition for applying said output voltage to said driving circuit means to brake said motor.

4. A drive control circuit for a brushless DC motor comprising bidirectional-rotation driving circuit means for applying current in either of two opposite directions to said motor; servo circuit means providing a servo output signal for said driving circuit means to control the phase and speed of said motor; rotation detecting means for providing a phase signal whose magnitude and polarity indicate the electrical rotational angle of said motor, said rotation detecting means including sensor means providing said phase signal even if said motor is not rotating; amplifier means amplifying said phase signal and providing an output voltage that varies according to said phase signal; and controllable switching means having a first condition for normally providing said servo output signal to said driving circuit means, and a second condition for applying said output voltage to said driving circuit means to brake said motor.

5. A drive control circuit according to claim 4, wherein said sensor means includes a Hall element.

6. A drive control circuit according to claim 4, wherein said sensor means includes a magnetoresistive element.

7. A drive control circuit for a brushless DC motor comprising bidirectional-rotation driving circuit means for applying current in either of two opposite directions to said motor; servo circuit means providing a servo output signal for said driving circuit means to control the phase and speed of said motor; first rotation, detecting means for providing a first phase signal whose magnitude and polarity indicate the electrical rotational angle of said motor; second rotation detecting means for providing a second phase signal whose magnitude and polarity indicate an electrical rotational angle of said motor displaced by an electrical angle of an odd multiple of $\pi/2$ from that indicated by said first phase signal; amplifier means amplifying said first phase signal and providing a first output voltage that varies with said first phase signal and a second output voltage that varies inversely therewith; comparator means coupled to said second rotation detecting means for comparing said second phase signal with a reference level to provide a switching signal; first switching means having inputs coupled to receive said first and second output voltages, and switched over by said switching signal to provide a switched output signal; and second switching means having a first condition for normally providing said servo output signal to said driving circuit means, and a second condition for applying said switched output voltage to said driving circuit means to brake said motor.

8. A drive control circuit according to claim 7, wherein said amplifier means includes a first operational amplifier connected as a non-inverting amplifier with an input thereof connected to said first rotation detecting means and an output thereof connected to one input of the first switching means, and a second operational amplifier connected as an inverting amplifier with an input thereof connected to said first rotation detecting means and an output thereof connected to another input of the first switching means.

9. A drive control circuit according to claim 7, wherein said comparator means includes an operational amplifier having a minus input coupled to said second rotation detecting means and a plus input connected to a reference voltage.

10. A drive control circuit according to claim 9, wherein said comparator means further includes a variable resistor having a resistive element bridged between two reference potentials and a slider coupled to said plus input.

11. A drive control circuit for a brushless DC motor comprising bidirectional-rotation driving circuit means for applying current in either of two opposite directions to said motor; servo circuit means providing a servo output signal for said driving circuit means to control the phase and speed of said motor; first rotation detecting means for providing a first phase signal whose magnitude and polarity indicates the electrical rotational angle of said motor; second rotation detecting means for providing a second phase signal whose magnitude and polarity indicate an electrical rotational angle of said motor displaced by an electrical angle of an odd multiple of $\pi/2$ from that indicated by said first phase signal; amplifier means coupled to receive said first and second phase signals and providing a first output voltage corresponding to the difference between said first and second phase signals and a second output voltage that varies inversely with said first output voltage; comparator means coupled to said first and second rotation detecting means for comparing a sum of said first and second phase signals to a reference level and providing a switching signal; first switching means having inputs coupled to receive said first and second output voltages and switched over by said switching signal to provide a switched output signal; and second switching means having a first condition for normally providing said servo output signal to said driving circuit means, and a second condition for applying said switching output voltage to said driving circuit means to brake said motor.

12. A drive control circuit according to claim 11, wherein said amplifier means includes a differential amplifier having first and second inputs coupled to receive said first and second phase signals, respectively, and an output providing said first output voltage.

13. A drive control circuit according to claim 12, wherein said amplifier means further includes an inverter amplifier having an input coupled to the output of said differential amplifier and an output providing said second output voltage.

14. A drive control circuit according to claim 11, wherein said comparator means includes an operational amplifier having a plus input, a minus input, and an output; a reference voltage source coupled to said plus input; and a resistive adder network coupling said first and said second rotation detecting means to said minus input; with the output of said operational amplifier providing said switching signal.

15. A drive control circuit according to claim 14, wherein said reference voltage source includes a variable resistance having a resistive element bridging between two voltage sources and a slider coupled to said plus terminal.

* * * * *